United States Patent [19]

Sauer et al.

[11] Patent Number: 5,520,702
[45] Date of Patent: May 28, 1996

[54] METHOD AND APPARATUS FOR APPLYING A CINCH MEMBER TO THE ENDS OF A SUTURE

[75] Inventors: Jude S. Sauer, Pittsford; Louis N. Rapp, Dansville; Thomas A. Tiberio, Rochester, all of N.Y.

[73] Assignee: United States Surgical Corporation, Norwalk, Conn.

[21] Appl. No.: 201,289

[22] Filed: Feb. 24, 1994

[51] Int. Cl.$^6$ .................................................. A61B 17/04
[52] U.S. Cl. .................. 606/144; 606/139; 606/148; 29/751; 29/812; 72/409.08; 411/495
[58] Field of Search .............. 606/139, 142–148; 29/270, 272, 280, 283.5, 751, 752, 812; 72/410, 411, 415, 420, 409; 411/495, 447

[56] References Cited

U.S. PATENT DOCUMENTS

| | | |
|---|---|---|
| 3,016,056 | 1/1962 | Jacobs . |
| 3,664,345 | 5/1972 | Dabbs et al. . |
| 3,753,438 | 8/1973 | Wood et al. . |
| 3,910,281 | 10/1975 | Kletschka et al. . |
| 3,976,079 | 8/1976 | Samuels et al. . |
| 4,173,067 | 11/1979 | Steiner et al. ............................ 29/816 |
| 4,201,314 | 5/1980 | Samuels ................................... 29/816 |
| 4,291,698 | 9/1981 | Fuchs et al. . |
| 4,705,040 | 10/1987 | Mueller et al. . |
| 4,950,285 | 8/1990 | Wilk . |
| 4,953,384 | 9/1990 | Baillet et al. ............................ 29/751 |
| 4,955,913 | 9/1990 | Robinson . |
| 5,009,663 | 4/1991 | Broomé . |
| 5,053,047 | 10/1991 | Yoon . |
| 5,074,874 | 12/1991 | Yoon et al. . |
| 5,078,731 | 1/1992 | Hayhurst . |
| 5,085,661 | 2/1992 | Moss . |
| 5,105,648 | 4/1992 | Steiner et al. ............................ 29/751 |
| 5,111,681 | 5/1992 | Yasui et al. ............................... 29/751 |
| 5,116,340 | 5/1992 | Songer ...................................... 29/751 |
| 5,123,913 | 6/1992 | Wilk et al. . |
| 5,160,339 | 11/1992 | Chen et al. . |
| 5,219,359 | 6/1993 | McQuilkin et al. . |
| 5,274,903 | 1/1994 | Grois et al. ............................. 29/282 |
| 5,405,354 | 4/1995 | Sarrett . |
| 5,423,860 | 6/1995 | Lizardi et al. . |

FOREIGN PATENT DOCUMENTS

| | | |
|---|---|---|
| 2682867 | 10/1991 | France . |
| WO/9314701 | 1/1992 | WIPO . |
| WO9309721 | 7/1992 | WIPO . |

*Primary Examiner*—Gary Jackson

[57] ABSTRACT

A surgical apparatus and method of use is provided for applying and maintaining a securing member upon a length of suture material which extends from body tissue. The apparatus essentially comprises a handle assembly, and elongated housing extending distally from the handle assembly and a tool assembly preferably detachably connected to a distal end of the body portion and remotely operable from the handle. The tool assembly enables a surgeon to compress and maintain a securing member upon suture material in the body cavity while also providing means to cut unsecured suture material which extends from the compressed securing member. Additionally, an instrumentation kit is provided which includes the surgical apparatus and at least one additional tool assembly, as mentioned above, in cooperation with a top cover portion and a bottom cover portion.

20 Claims, 13 Drawing Sheets

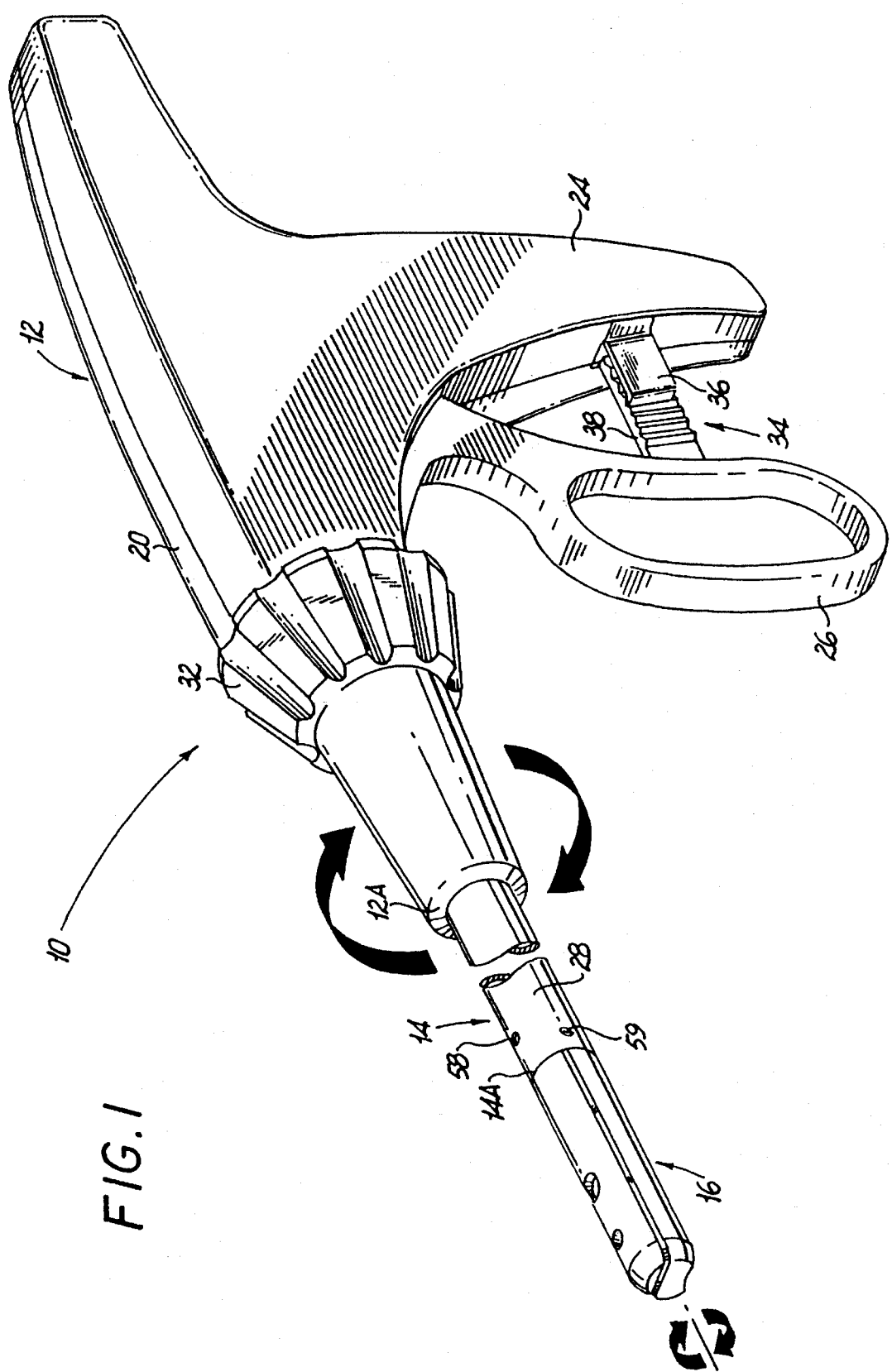

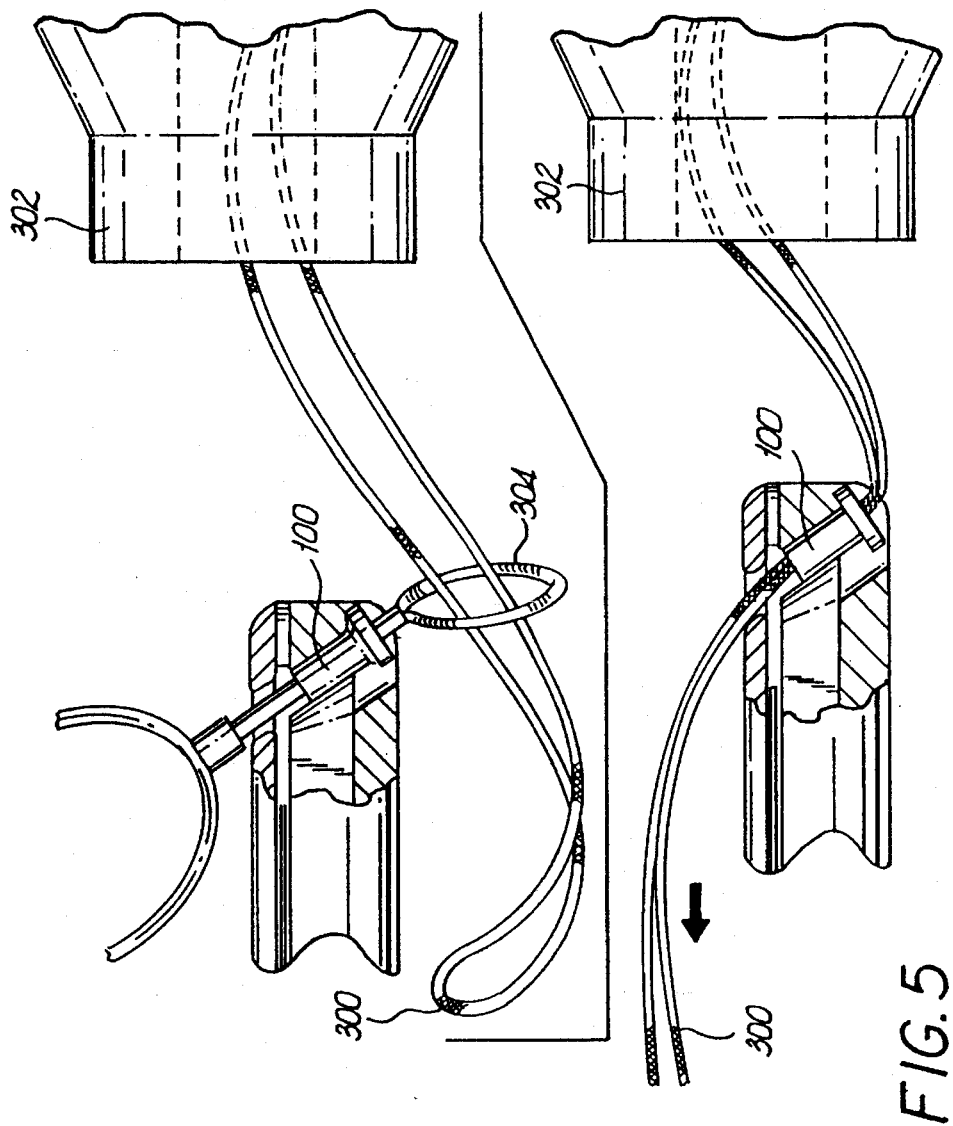
FIG. 4
FIG. 5
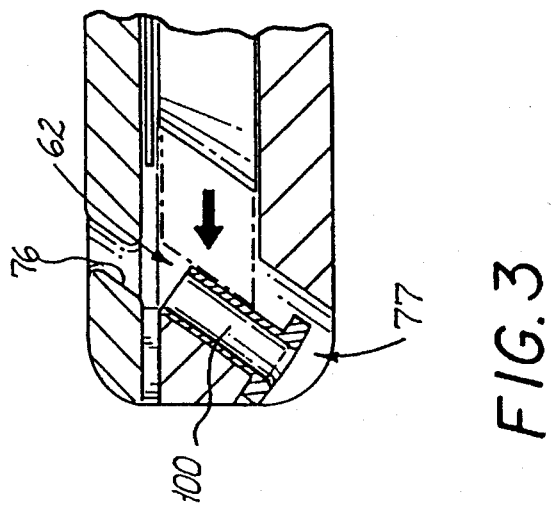
FIG. 3

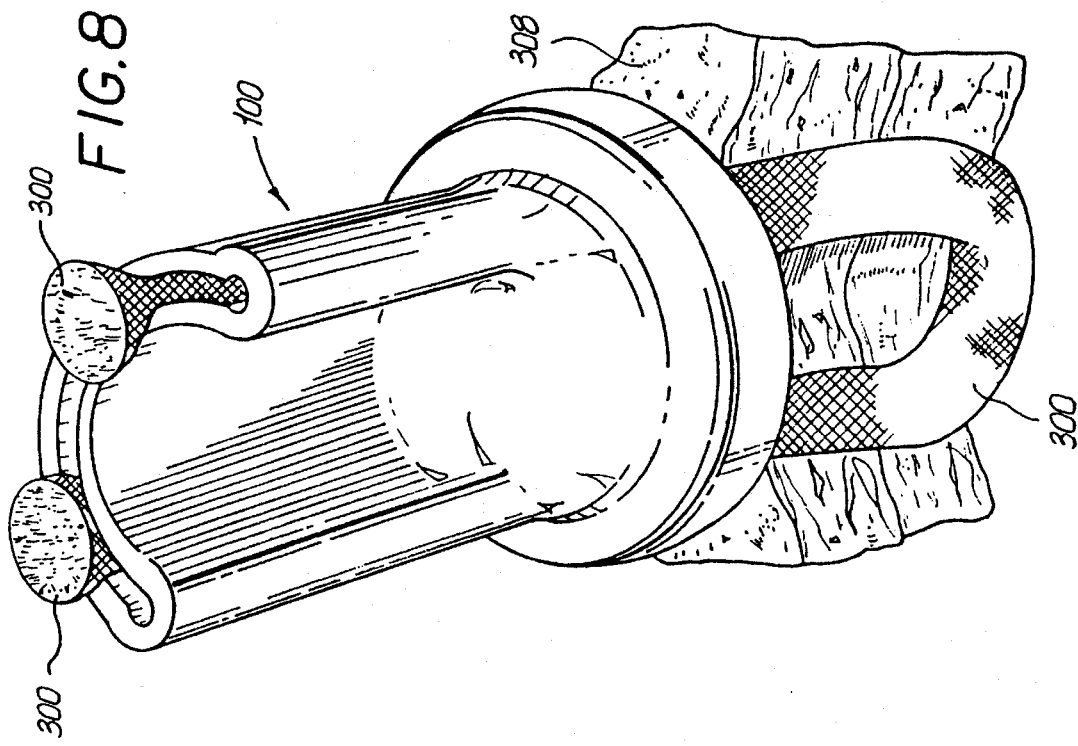
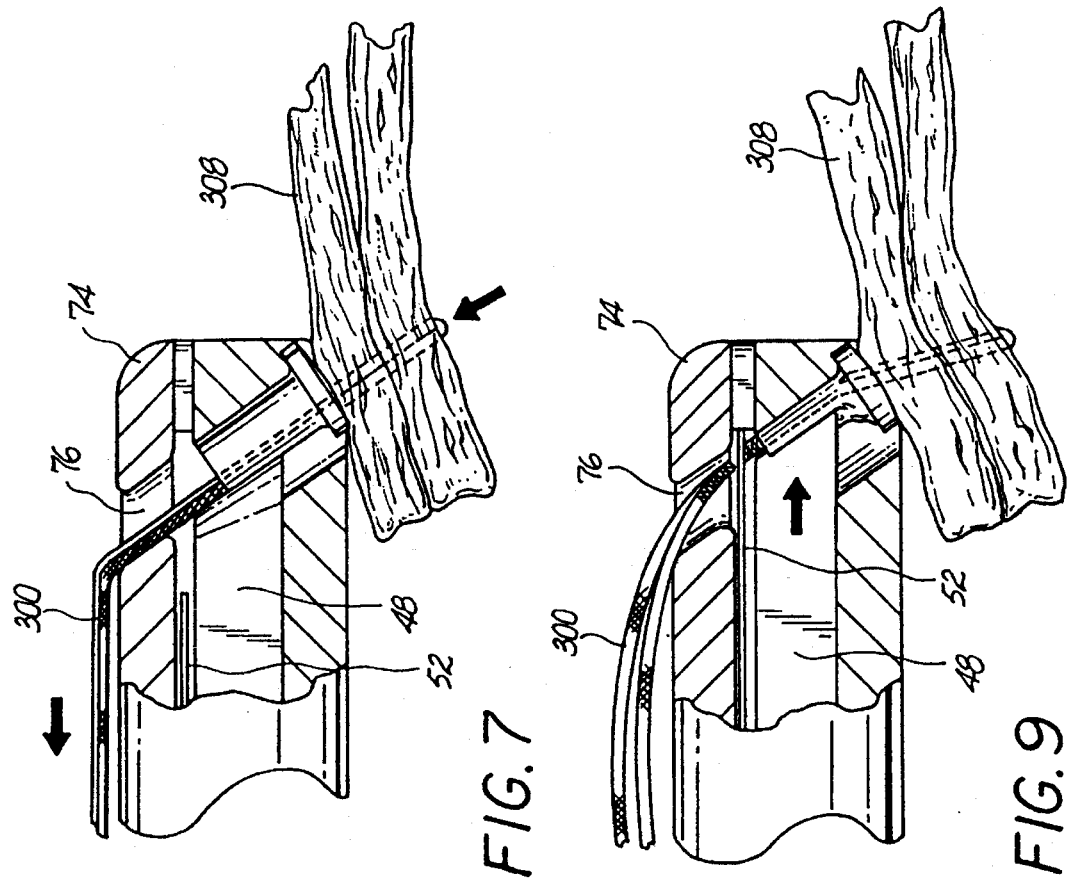

METHOD AND APPARATUS FOR APPLYING A CINCH MEMBER TO THE ENDS OF A SUTURE

BACKGROUND OF THE INVENTION

1. Field of the Invention

The subject invention relates to a surgical apparatus and method for the securing of sutures.

2. Description of the Related Art

As medical and hospital costs continue to increase, surgeons are constantly striving to develop advanced surgical techniques. Advances in the surgical field are often related to the development of operative techniques which involve less invasive surgical procedures and reduce overall patient trauma. In this manner, the length of hospital stays can be significantly reduced, and, therefore, the hospital and medical costs can be reduced as well.

One of the truly great advances in recent years to reduce the invasiveness of surgical procedures is endoscopic surgery. Generally, endoscopic surgery involves incising through body walls for example, viewing and/or operating on the ovaries, uterus, gall bladder, bowels, kidneys, appendix, etc. There are many common endoscopic surgical procedures, including arthroscopy, laparoscopy (pelviscopy), gastroentroscopy and laryngobronchoscopy, for example. Typically, trocars are utilized for creating the incisions through which the endoscopic surgery is performed. Trocar tubes or cannula devices are extended into and left in place in the abdominal wall to provide access for endoscopic surgical tools. A camera or endoscope is inserted through a relatively large diameter trocar tube which is generally located at the naval incision, and permits the visual inspection and magnification of the body cavity. The surgeon can then perform diagnostic and therapeutic procedures at the surgical site with the aid of specialized instrumentation, such as, forceps, cutters, applicators, and the like which are designed to fit through additional cannulas. Thus, instead of a large incision (typically 12 inches or larger) that cuts through major muscles, patients undergoing endoscopic surgery receive more cosmetically appealing incisions, between 5 and 10 millimeters in size. Recovery is, therefore, much quicker and patients require less anesthesia than traditional surgery. In addition, because the surgical field is greatly magnified, surgeons are better able to dissect blood vessels and control blood loss. Heat and water loss are greatly reduced as a result of the smaller incisions.

In many surgical procedures, including those involved in endoscopic surgery, it is often necessary to suture bodily organs or tissue. The latter is especially challenging during endoscopic surgery because of the small openings through which the suturing of bodily organs or tissues must be accomplished.

In the past, suturing of bodily organs or tissue through endoscopic surgery was achieved through the use of a sharp metal suture needle which had attached at one of its ends a length of suture material. The surgeon would cause the suture needle to penetrate and pass through bodily tissue, pulling the suture material through the bodily tissue. Once the suture material was pulled through the bodily tissue, the surgeon proceeded to tie a knot in the suture material. The knotting of the suture material allowed the surgeon to adjust the tension on the suture material to accommodate the particular tissue being sutured and control approximation, occlusion, attachment or other conditions of the tissue. The ability to control tension is extremely important to the surgeon regardless of the type of surgical procedure being performed.

However, during endoscopic surgery, knotting of the suture material is time consuming and burdensome due to the difficult maneuvers and manipulation which are required through the small endoscopic openings.

Many attempts have been made to provide devices to overcome the disadvantages of conventional suturing. Such prior art devices have essentially been staples, clips, clamps or other fasteners. U.S. Pat. Nos. 5,041,129 to Hayhurst et at., 5,080,663 to Mills et al., 5,021,059 to Kensy et al., 4,841,888 to Mills et al., 4,741,330 to Hayhurst, 4,724,840 to McVay et at., 4,705,040 to Mueller et al., 4,669,473 to Richards et al., 4,627,437 to Bedi et al., 4,448,194 to DiGiovanni et al., 4,039,078 to Bone, 4,235,238 to Ogiv et al., 4,006,747 to Kronenthal et al., 3,875,648 to Bone and 5,085,661 to Moss are representative of such prior art devices for use in place of conventional suturing. However, none of the above listed devices overcome the disadvantages associated with suturing bodily tissue during endoscopic surgery.

Accordingly, there is a need for a new and improved suture securing device to overcome the shortcomings and drawbacks of the above-mentioned prior art apparatus.

SUMMARY OF THE INVENTION

Because endoscopic procedures are more common than laparoscopic procedures, the present invention shall be discussed in terms of endoscopic procedures and apparatus. However, use herein of terms such as "endoscopic", "endoscopically", and "endoscopic portion", among others, should not be construed to limit the present invention to apparatus for use only in conjunction with an endoscopic tube. To the contrary, it is believed that the present invention may find use in procedures wherein access is limited to a small incision, such as, for example, arthroscopic procedures.

The present invention provides a novel surgical apparatus for securing the ends of a suture, and more particularly, for compressing a securing member about a loop of suture material. Briefly, the present invention enables the surgeon to bring about a desired tension upon a length of suture material, and maintain that tension by compressing a securing member upon the suture material thus replacing the need for knotting the suture material.

The surgical apparatus of the present invention includes a handle assembly having actuation structure and an elongated body potion extending from the handle assembly. An atraumatic tool assembly is connected to a distal end portion of the elongated body portion for compressing a preformed securing member. The atraumatic tool assembly is remotely operable from the handle assembly for enclosing and compressing a securing member. The apparatus may also include a cutting blade for curing a length of suture material which extends from the compressed securing member.

In one method of use, first the surgeon connects a tool assembly having a securing member releasably disposed in the elongated body portion and brings the two ends of a suture extracorporeally, via a cannula assembly which enables the surgeon to thread the suture ends through the securing member using a conventional threading tool. The surgeon, while grasping the ends of the suture threaded through the securing member, inserts the tool assembly and a portion of the endoscopic body into the body cavity, via a cannula assembly, into approximation with body tissue having the sutures extending therefrom. In some embodiments of the present invention, threading can be accomplished intracorporeally.

The surgeon then gently pulls on the suture ends extending from the body cavity so as to bring the desired tissue pieces together therein pushing the securing member toward the tissue and tensioning the suture material extending from the body tissue. The surgeon then deforms the securing member by squeezing the handle of the instrument. In the embodiment having a cuffing member, further pressure applied to the handle actuates a cutting member in the tool assembly to cut the unsecured lengths of suture material extending from the compressed securing member, otherwise, the suture is cut with a separate cutting instrument. Thereafter, the deformed securing member is released from the tool assembly.

Finally, the surgeon removes the tool assembly from the body cavity, via a cannula assembly, and disengages the tool assembly from the elongated body portion. A new tool assembly having a securing member releasably disposed therein may then be detachably connected to the elongated body portion therein enabling the repetition of the above described method.

Further, the present invention provides a surgical instrumentation kit including the equipment for compressing a securing member upon a length of suture material during a surgical procedure.

The surgical apparatus, method and kit of the present invention is particularly adapted for use during endoscopic surgical techniques. However, it is to be appreciated that the surgical apparatus, method and kit of the present invention can be used during any operative procedure requiring the suturing of bodily tissue or organ parts.

Further features of the surgical apparatus of the subject invention will become more readily apparent from the following detailed description of the invention taken in conjunction with the accompanying drawings.

BRIEF DESCRIPTION OF THE DRAWINGS

The surgical apparatus of the subject invention will be described hereinbelow with respect to the drawings wherein:

FIG. 1 is a perspective view of a surgical apparatus of the subject invention;

FIG. 3 is a cross-sectional view of the distal end portion of the tool assembly having a securing member releasably disposed therein;

FIG. 4 is a side elevational view in partial cross-section of the distal end portion of the tool assembly illustrated in FIG. 3, wherein a threading device is shown capturing a suture for engagement in the securing member;

FIG. 5 is a side elevational view in partial cross-section of the distal end portion of the tool assembly illustrated in FIG. 3, wherein suture material is positioned within the securing member;

FIG. 7 is an enlarged side elevational view in partial cross-section of the distal end portion of the tool assembly in approximation with body tissue wherein suture material is positioned in the securing member;

FIG. 8 is a greatly enlarged perspective view of a compressed securing member with severed suture material secured therein;

FIG. 9 is an enlarged side elevational view in partial cross-section of the distal end of the surgical apparatus illustrated in FIG. 7, further illustrating the cutting blade cutting a length of suture material extending from a compressed securing member;

DETAILED DESCRIPTION OF THE PREFERRED EMBODIMENTS

Figure 1A:
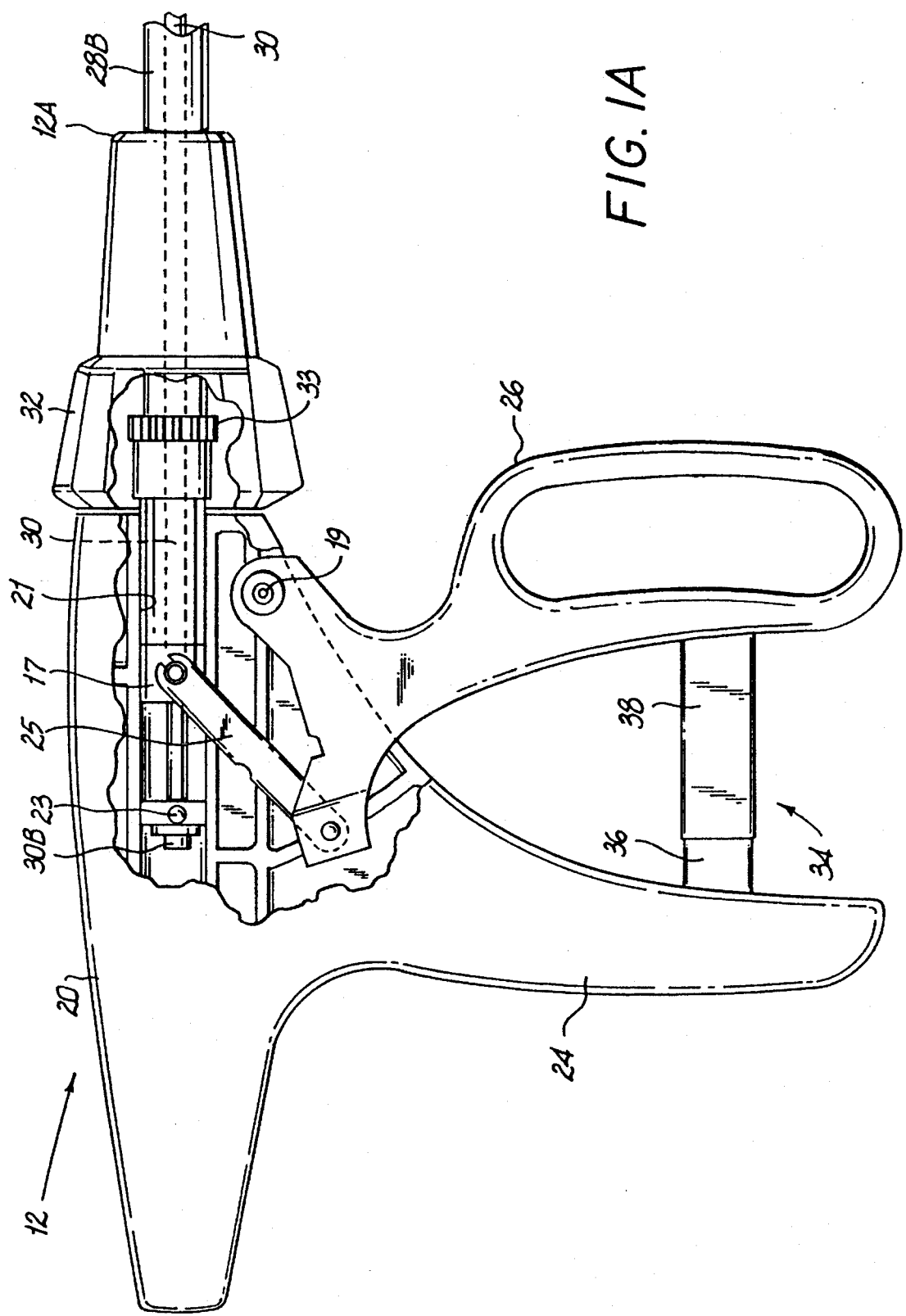
FIG. 1A is a side view of the handle assembly of the surgical apparatus of FIG. 1 with a portion of the handle body portion broken away.

In the drawings and in the description which follow, the term "proximal", as is traditional, will refer to the end of the surgical apparatus which is closest to the operator, while the term "distal" will refer to the end of the apparatus which is furthest from the operator.

Figure 6:
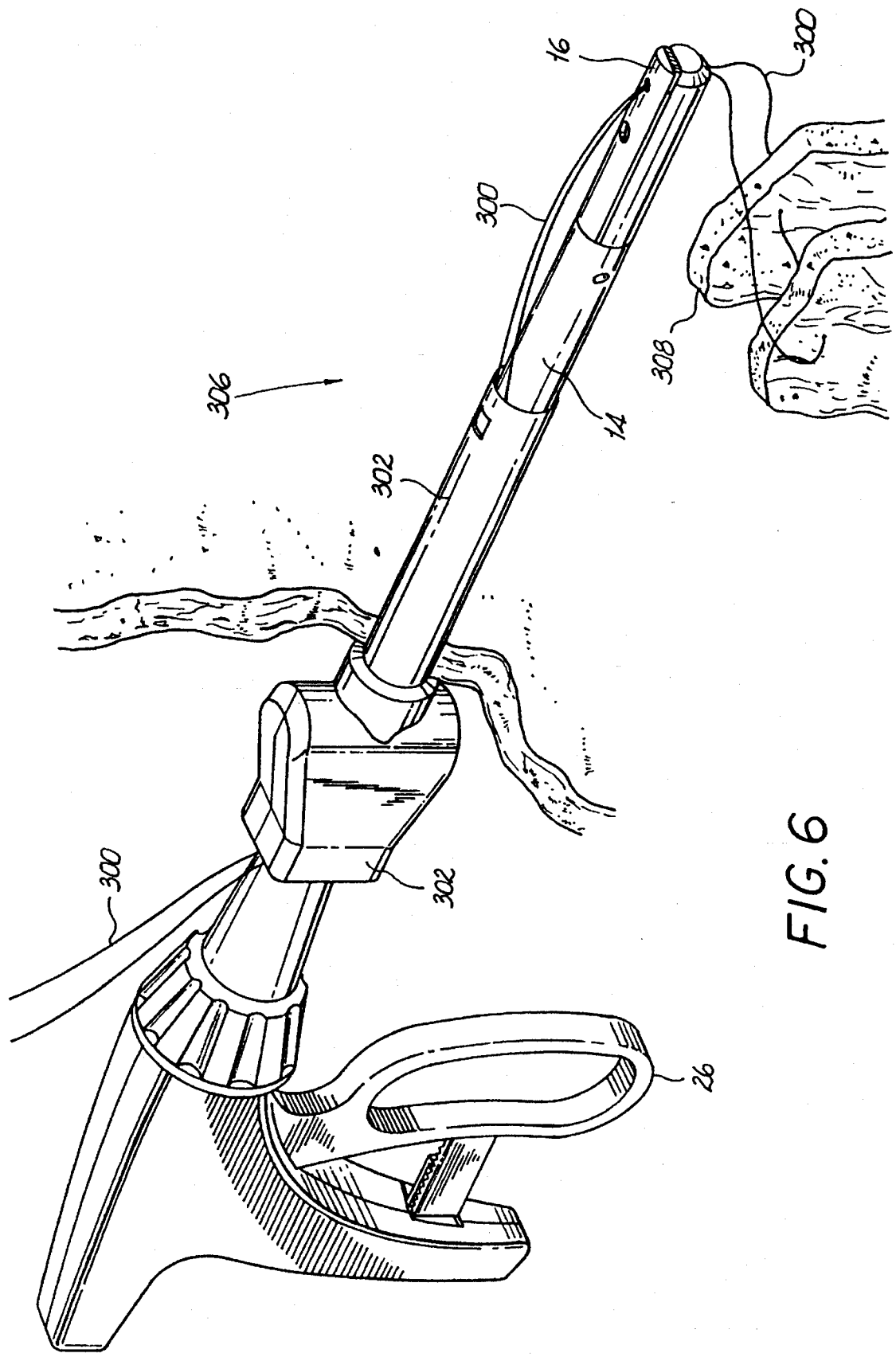
FIG. 6 is a perspective view of the surgical apparatus of the subject invention shown extending through a cannula assembly into the operative site wherein a suture material is engaged in a distal end of the surgical apparatus.

Referring now in specific detail to the drawings, in which like reference numbers identify similar or identical elements, FIG. 1 illustrates a preferred embodiment of a surgical apparatus, shown generally at 10. The surgical apparatus 10 includes a handle assembly 12 and an elongated body portion 14 extending distally from the handle assembly 12 and defining a longitudinal axis. A tool assembly 16 is operatively associated with a distal end portion of the elongated body portion 14 and is remotely operable by the handle assembly 12. A rotation knob 32 is provided to rotate the elongated body portion 14 about the longitudinal axis. A suture securing member is positioned at a distal end of the apparatus. The securing member is configured to receive one or more strands of suture and can then be deformed so as to secure that suture. The securing member may, however, take many different shapes, as will be described in more detail below. The embodiment of FIG. 1 is adapted to be particularly useful in endoscopic or laparoscopic procedures wherein the endoscopic portion of the surgical apparatus 10 is inserted into the operative site, via a cannula assembly (FIG. 6).

In reference to FIG. 1 and 1A, the handle assembly 12 includes a body portion 20 having a bore portion 21 extending from a distal end 12A thereof. The body portion 20 of the handle assembly 12 defines a stationary grip member 24 and includes a pivoting handle member 26 which is pivotably connected to the body portion 20 about the pivot point 19, so as to be pivotably movable in approximation with the stationary grip member 24.

As best seen in FIG. 1, an interengaging ratchet mechanism 34 may be provided to incrementally adjust and hold the position of the pivoting handle member 26. This incremental positioning, which sets the pivoting handle member 26 at various locations along its path of travel, provides a means to incrementally actuate the tool assembly 16 during the surgical procedure. The ratchet mechanism 34 includes interengaging racks 36, 38 which are respectively provided on the handles 24, 26. It is to be appreciated that the ratchet mechanism 34 may be positioned internally within the body portion 20 of the handle assembly 12 so that none of the mechanism is exposed to environmental conditions.

Figure 2:
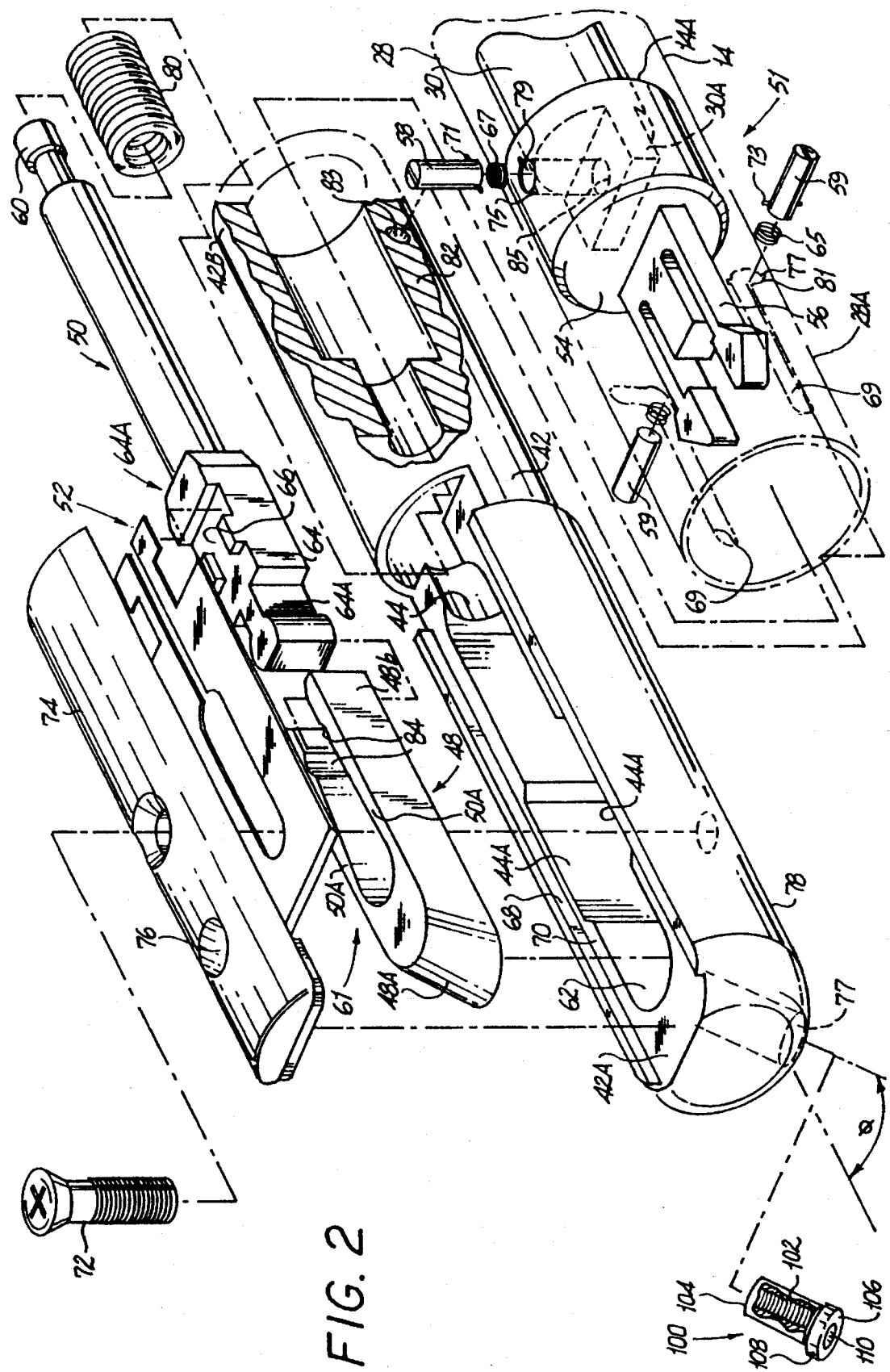
FIG. 2 is an exploded perspective view of the tool assembly of the surgical apparatus of FIG. 1.

Turning to FIGS. 1A and 2, the elongated body portion 14 includes an outer tubular member 28 and an inner rod member 30 slidably received therein. The inner rod member 30 is adapted for coaxial reciprocal motion within the outer tubular member 28. The proximal end 30B of the inner rod member 30 is attached to a coupling block 17 which is slidably mounted in the proximal end portion of the inner bore 21 defined in the body portion 20 of the handle assembly 12. A coupling lock mechanism 23 facilitates the attachment of the inner rod member 30 with the coupling block 17. A linkage member 25 connects the pivotable handle member 26 to the coupling block 17, such that, pivotable movement of the pivotable handle member 26 about pivot point 19 effectuates reciprocal coaxial movement of the coupling block 17 in the inner bore portion 21 of the handle assembly 12, which in turn, effectuates corresponding reciprocal coaxial movement of the inner rod member 30 in the outer tubular member 28 relative to the longitudinal axis of the elongated body portion 14. A proximal end portion 28B of the outer tubular member 28 attaches to the distal end portion 12A of the handle assembly 12.

In the embodiment illustrated in FIG. 1, the outer tubular member 28 and the tool assembly 16 engaged thereto, as will be described fully below, are axially rotatable by a rotation knob 32 rotatably mounted in the body portion 20 of the handle assembly 12. The rotation knob 32 engages a bushing 33 (FIG. 1A) attached to a proximal end portion 28B of the outer tubular member 28. The rotation knob 32 is preferably knurled or provided with ridges to allow for easy manipulation by the surgeon's thumb or fingers. Additionally, the bushing may be provided with angular faces of polygonal cross-section cooperating with corresponding races formed in the body portion 20 of the handle assembly 12 so as to provide predetermined rotational stops such that the tool assembly 16 is maintained at a given angular orientation relative to the handle assembly 12.

Returning to FIG. 2, the tool assembly 16 is specifically configured and dimensioned so as to be detachably connected to the distal end 14a of the elongated body portion 14. This allows for reloading of the instrument with a fresh suture securing member after the original assembly has been fired. This allows the surgeon to use the instrument multiple times in a single operation, simply by replacing the spent tool assembly. The tool assembly 16 includes an elongated tool housing 42 defining a central bore 44 extending therethrough which is open at a proximal end 42b of the tool housing 42. Slidably received in the central bore 44 of the tool housing 42 is a hammer element 48, a push rod member 50 and a cutting blade 52.

An engaging assembly 51 is provided in cooperation with the tool housing 42 and the elongated body portion 14 so as to facilitate the detachable engagement between the tool assembly 16 and the elongated body portion 14. The engaging assembly 51 comprises a coupling block 54 which includes a clip member 56 extending from a distal end thereof. The clip member 56 is dimensioned and configured to attach to a coupling member 60 which extends from the proximal end of the push rod member 50, such that coaxial reciprocal motion of the inner rod member 30 effectuates corresponding coaxial reciprocal motion of the push rod member 50 relative to the elongated body portion 42 of the tool assembly 16. A coupling pin 58 attaches the coupling block 54 to the distal end 30a of the inner rod member 30.

Coupling pins 59 are 180 degrees apart and are located on wall 82 of the tool assembly. Matching "J"-shaped slots 69 are cut into the distal end portion of the outer tubular member 28A so that when the pins 59 are aligned with slots 69 and pushed proximally into these slots, the tool assembly is attached and secured to the body assembly. A compliant seal (not shown) is located between the tool assembly 16 and the distal end of the outer tubular member 28A. When the tool assembly 16 is attached to the outer tubular member 28 as described above, the seal compresses, and the tool assembly can be rotated so that the pins 59 seat in the bent portion of the J-shaped slots. To release the tool assembly, the assembly is rotated in the opposite direction, releasing the pins from the bent portion of the J slot and freeing the tool assembly to be removed from the outer tubular member 28. While the tool assembly 16 is engaged, the prongs of clip member 56 are contained in the proximal-most bore of housing 42, aiding in the attachment of clip member 56 to coupling member 60.

A deforming assembly 61 is disposed in tool assembly 16 and is configured to compress a securing member 100 releasably disposed in the central bore portion 44 of the tool housing 42 about a length of suture material extending from body tissue. Thus, compression of the securing member effectively cinches the suture to maintain tension on the suture, as will be described below. The deforming assembly 61 includes a hammer element 48, a push rod member 50 as well as an anvil cutout portion 62 which is defined in a distal end portion 42A of the tool housing 42. In particular, the push rod member 50 is provided with a push rod block 64 at a distal end thereof which abuts against a proximal end 48b of the hammer element 48 and is dimensioned and configured for reception into the proximal end portion 48b of the hammer element 48. The hammer element 48 is provided with a substantially rounded distal end 48a inclined at an acute angle corresponding to the angle of inclination ø of aperture 77. This angle ø can range from 0° to less than 180° and is, preferably about 55°, relative to the longitudinal axis of the elongated body portion 14. The proximal end portion 48b of the hammer element 48 is provided with opposing expandable arms 50 which are configured to expand into the expansion cutouts 44A provided in the central bore 44 of the tool housing 42 when the distal end portion 64A of the push rod block 64 is received therein.

A cutting blade 52 is mounted along the top surface 66 of the push rod block 64 and is dimensioned and configured for reciprocal motion along a cutout portion 68 defined along the top surface 70 of the tool housing 42. A threaded screw 72 mounts a blade cover 74 atop the top surface 70 of the tool housing 42. The blade cover 74 is provided with an aperture 76 which is in alignment with the securing member 100 releasably disposed in the anvil portion 62 of the tool housing 42.

Figure 10:
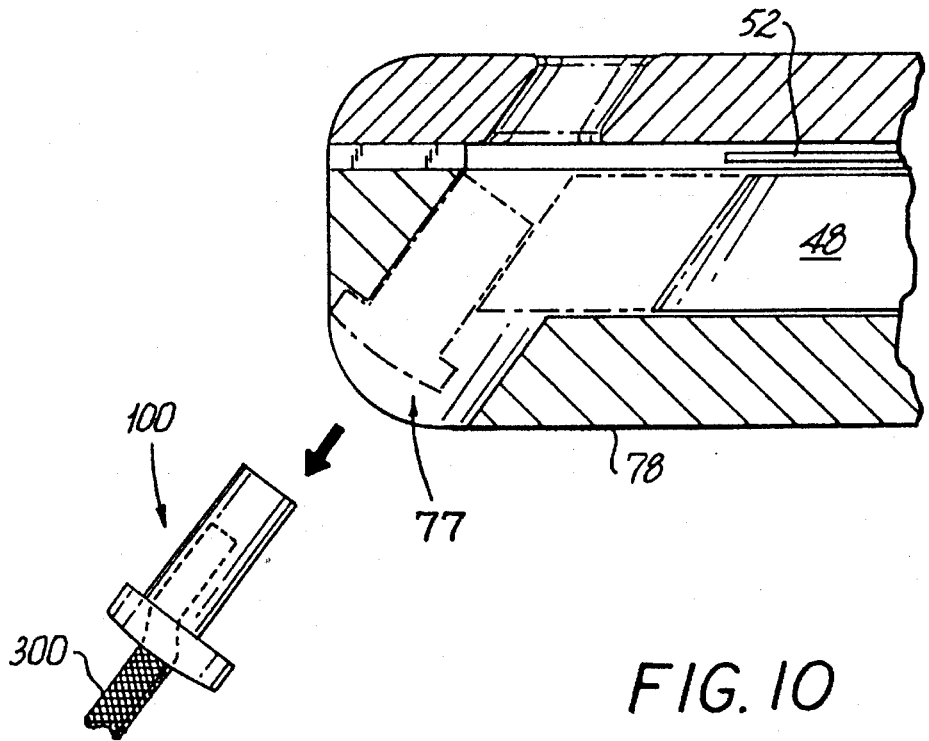
FIG. 10 is a cross-sectional view of the distal end portion of the tool assembly illustrating the securing member being released from the tool assembly.
Figure 11:
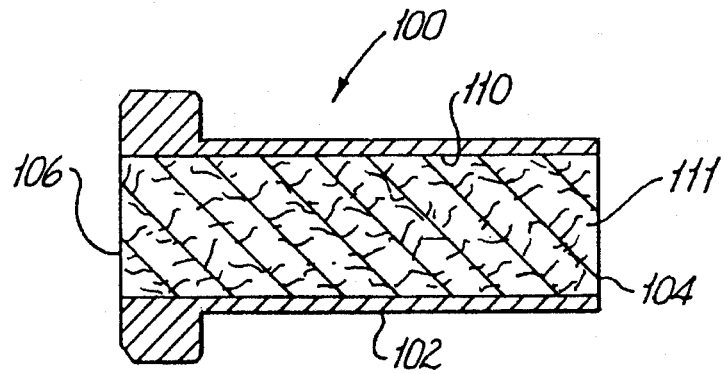
FIG. 11 is an enlarged side view in cross section of a preferred securing member in accordance with the present invention.
Figure 11A:
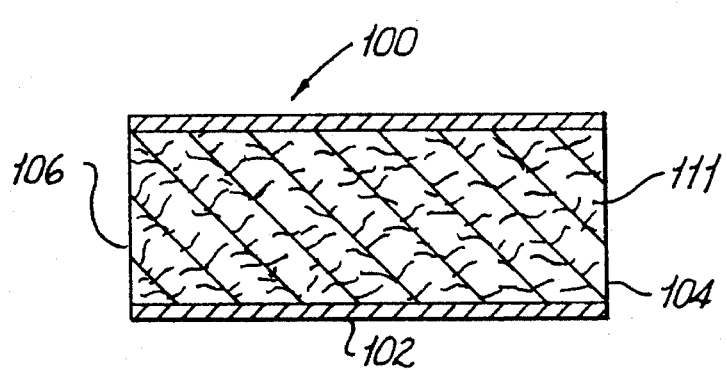
FIG. 11A is an enlarged view of an alternate embodiment of the securing member in accordance with the present invention.

Referring to FIGS. 2, 10 and 11, the securing member 100 is a cylindrical member 102 having first and second opposed ends 104, 106. The securing member 100 includes an outer compressible surface defining an inner bore 110 extending between the opposed first and second ends 104, 106. At least one of either of the first or second ends 104, 106 is formed with an atraumatic configuration. Preferably, the atraumatic configuration is on the end which is disposed adjacent body tissue 300. The atraumatic configured end 106 is preferably defined by a mushroom shaped configuration, as best shown in FIGS. 2 and 11. Additionally, the inner bore portion 110 of the securing member 100 may preferably be provided with a textured surface 111 so as to enhance the connection between a length of suture material 300 and the compressed securing member (FIG. 8).

Closed-wall securing member 100 is positioned adjacent the anvil portion 62 through an aperture 77 which is provided on the bottom surface 78 of the tool housing 42 (FIG. 3). The securing member 100 is releasably disposed in the anvil portion 62 at an acute angle, preferably 55°, relative to the longitudinal axis of the elongated body portion 14.

The distal end 48A of the hammer element 48 normally biases the securing member 100 against the anvil portion 62 of the tool housing 42 without deformation so as to prevent the securing member 100 from releasing from the anvil portion 62 and subsequently falling out of aperture 77. An assist spring 82 is disposed intermediate a retaining wall 82 defined in the central bore 44 of the tool housing 42 and between a proximal end 64a of the push rod block 64 so as to facilitate the normal biasing force of the distal end 48A of the hammer element 48 against the securing member 100 releasably disposed in aperture 77.

The securing member 100 is fabricated from a biocompatible material and is preferably formed of a non-bioabsorbable material, such as titanium. Alternatively, the securing member 100 may be fabricated from a bioabsorbable polymer comprising a homopolymer, copolymer or a blend obtained from one or more monomers selected from the group consisting of glycolide, glycolic acid, lactide, lactic acid, p-dioxanone, E-caprolactone and trimethylene carbonate.

Figure 13:
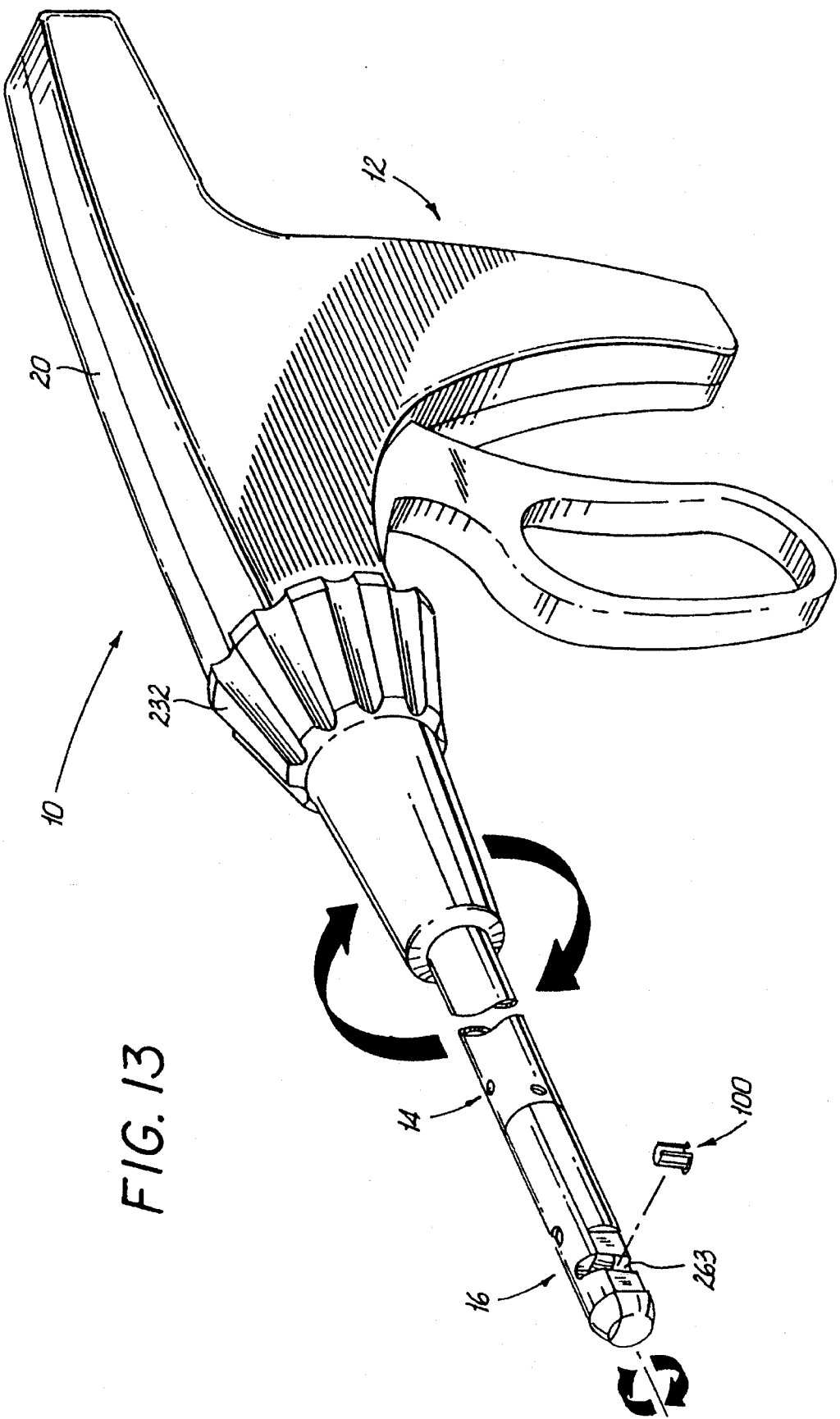
FIG. 13 is a perspective view of an alternate embodiment of the surgical apparatus of the subject invention.
Figure 17:
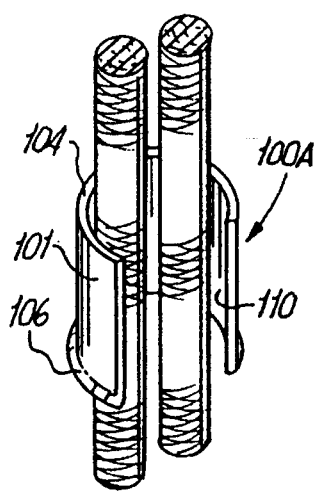
FIGS. 17–20 are each perspective views of alternative securing members suitable for use with the surgical apparatus of FIG. 13.

An alternate embodiment of the securing member is shown in FIG. 17. The securing member 100A is "open-walled" and is defined by an elongated member which comprises first and second opposed ends 104, 106. The open-walled securing member 100A includes an outer compressible surface 101 which defines an elongated U-shaped inner channel 110 extending between the opposed first and second ends 104 and 106. The elongated U-shaped inner channel 110 may be provided with a textured surface (not shown) so as to enhance the connection between a length of suture material 300 and the compressed open-walled securing member 100A (FIG. 13). This open-walled configuration enables the suture to be placed within the confines of the securing member via a side wall rather than being threaded through the bottom portion (or top portion) as in the "closed wall" configuration of FIG. 11.

Figure 18:
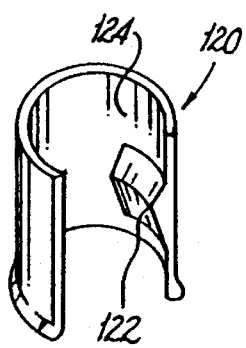
Figure 19:
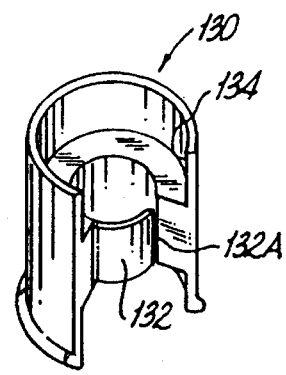
Figure 20:
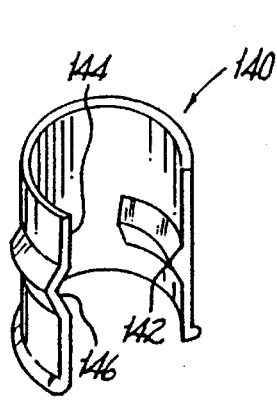
Figure 21:
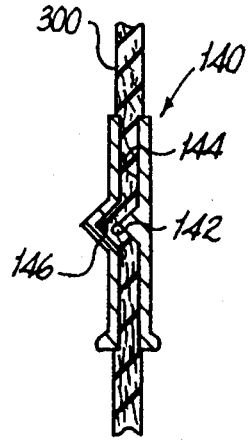
FIG. 21 is a cross-sectional view of the securing member of FIG. 20 shown deformed with a length of suture secured therein.
Figure 22:
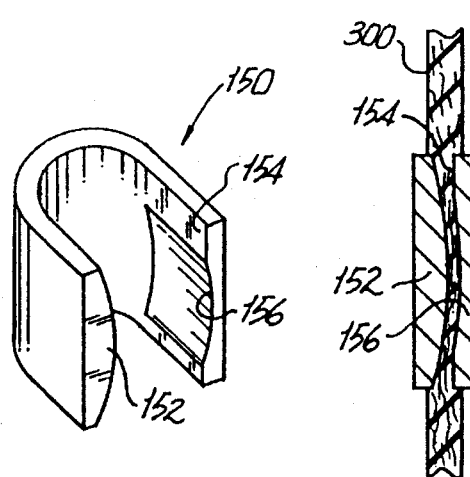
FIG. 22 is a perspective view of yet another securing member suitable for use with the surgical apparatus of FIG. 13.
Figure 23:
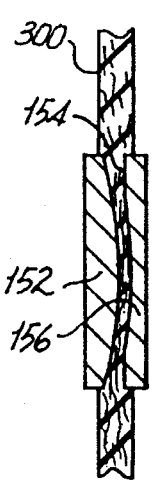
FIG. 23 is a cross-sectional view of the securing member of FIG. 22 shown deformed with a length of suture secured therein.

FIG. 18 illustrates an alternate open-walled securing member 120 provided with an elongated surface 122 projecting radially inward in the inner channel 124 of the open-walled securing member 120 for enhancing the connection between the securing member 120 and a length of suture material 300 extending therethrough (not shown). FIG. 19 illustrates a open-walled securing member 130 provided with a resilient door 132 in the inner channel 134 of the securing member 130. The resilient door 132 is dimensioned and configured to allow for threading of the suture by passing the suture through the non-hinged surface of the door 132A and to inwardly deflect during the reception of a length of suture material into the inner channel 134 of the securing member 136 and thereafter functioning to help restrain the length of suture material from moving outward from the inner channel 134 of the open-walled securing member 130. FIG. 20 illustrates a open-walled securing member 140 provided with an elongated surface 142 in the inner channel portion 144 dimensioned and configured for reception into a corresponding groove 146 defined in the inner channel portion 144 of the securing member 140. As illustrated in FIG. 21, the elongated projecting surface 142, together with the corresponding groove 144, facilitate an enhanced connection between a compressed open-walled securing member 140 and a length of suture material 300 extending therethrough by creating a non linear path for the crimped surface. FIG. 22 illustrates a open-walled securing member 150 being provided with a rounded projection 152 in the inner channel portion 154 dimensioned and configured for reception into correspondingly dimensioned and configured depression 156 defined in the inner channel portion 154. Thus, as illustrated in FIG. 23, the rounded projection 152 and depression portion 156 of the inner channel 154 facilitate an enhanced connection between a compressed open-wailed securing member 150 and a length of suture material 300 extending therethrough. Clearly, other shapes and configurations for the securing member are contemplated to aid in securing the suture.

Figure 14:
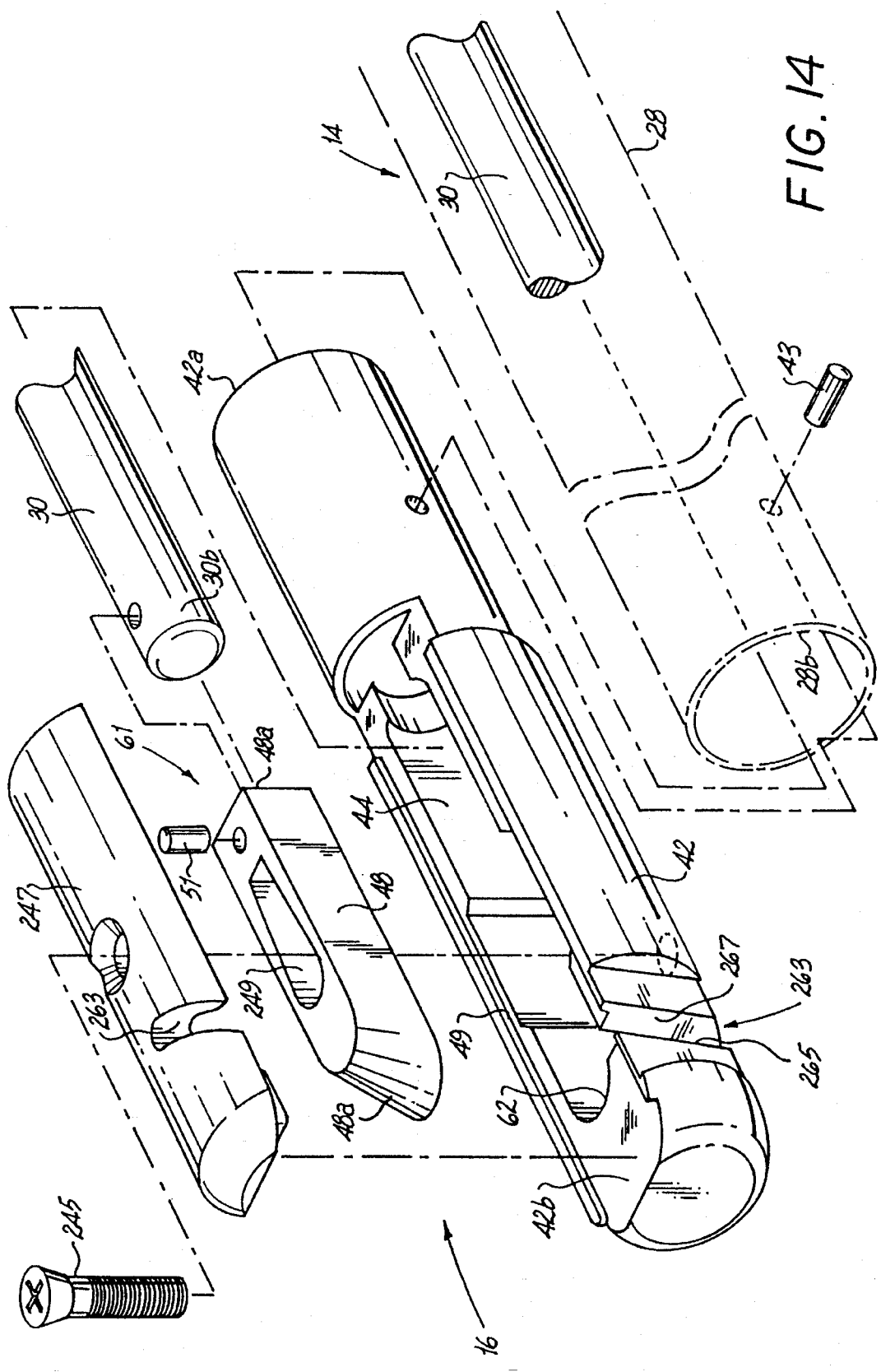
FIG. 14 is an exploded perspective view of the tool assembly of the surgical apparatus of FIG. 13.
Figure 15:
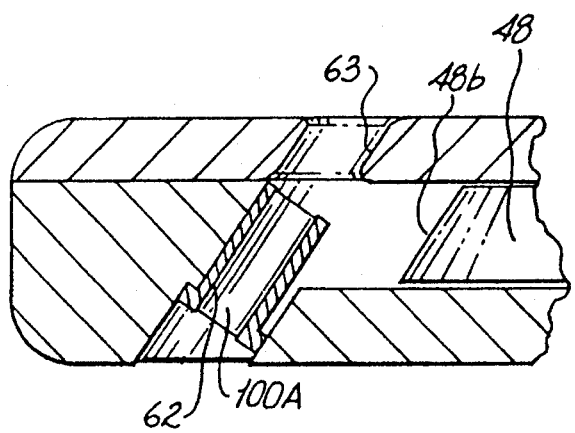
FIGS. 15 and 16 are cross-sectional views of the distal end portion of the tool assembly of the apparatus of FIG. 13.
Figure 16:
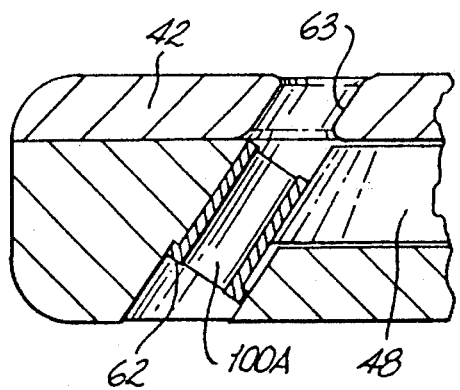
Figure 24:
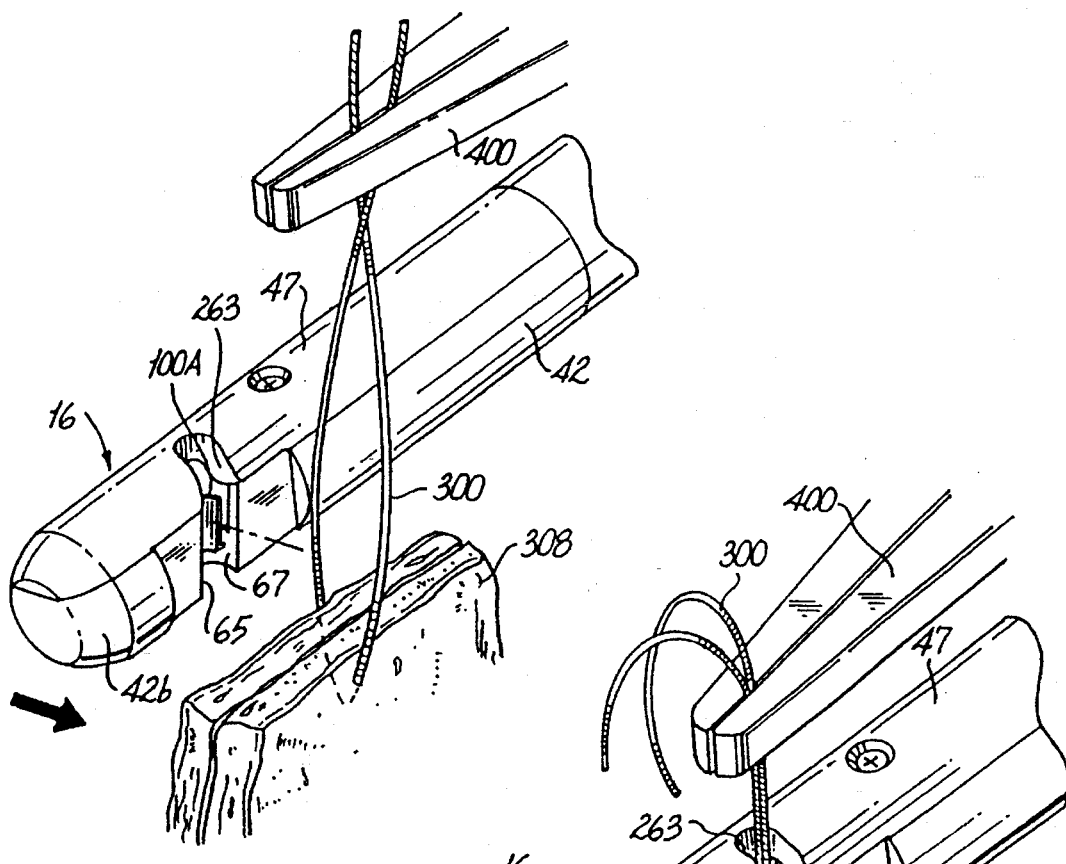
FIG. 24 is a perspective view of the tool assembly illustrated in FIG. 13 in close approximation with body tissue having suture material extending therefrom.

The threading channel 263 is preferably provided with elongated planar walls 265 and 267 which define the generally U-shaped inner channel 263 (FIGS. 14 and 24). Turing to FIG. 24, the threading channel 263 is defined in the distal end portion 42b of the tool housing 42 and is dimensioned and configured to releasably retain the open-walled securing member 100A. Further, the threading channel 263 is dimensioned and configured to receive a length of suture material 300 therein such that the length of suture material 300 may receive into the inner channel 110 of the open-walled securing member 100, via the threading channel 263. Thus, the suture can be inserted through the side of the tool and securing member.

Figure 25:
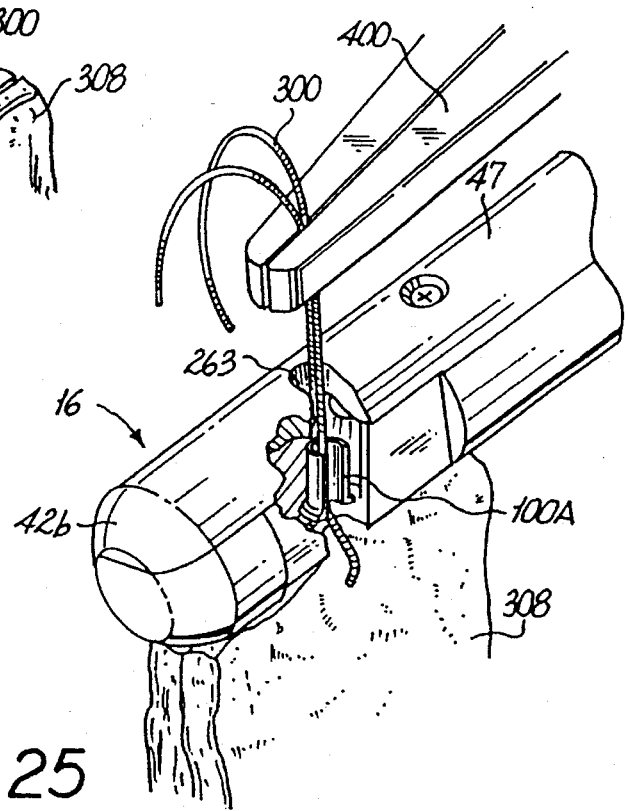
FIG. 25 is a perspective view of the tool assembly illustrated in FIG. 24, wherein the suture material extends through the open-walled securing member releasably disposed in the anvil portion of the tool assembly.

The open-walled securing member 100A is retained in the threading channel 263 adjacent the anvil portion 62 of the tool housing (FIG. 25). As with the closed-walled member, the open-walled securing member 100A is releasably disposed in the anvil portion 62 preferably at an acute angle relative to the longitudinal axis of the elongated body portion 14. The substantially rounded distal end 48a of the hammer element 48, the anvil portion 62 and the threading channel 263 are all preferably defined at a corresponding acute angle relative to the longitudinal axis of the elongated body portion. (See FIGS. 2 and 10.)

Turning now to the operation of the instrument and referring again to FIGS. 1 and 2, when the pivotable handle member 26 is actuated, this moves the inner rod member 30 distally from the handle assembly 12 which causes corresponding distal movement of the push rod member 50 relative to the longitudinal axis of the elongated body portion 14. Distal movement of the push rod member 50 causes the push rod block 64 to drive against the proximal end 48b of the hammer element 48 causing the hammer element 48 to drive distally into approximation with the anvil portion 62 therein causing the distal end 48A of the hammer element 48 to deform the securing member 100 (FIG. 7). At this point the hammer element 48 is bearing against anvil portion 62 and is thus restrained from further distal movement. It is also possible to cream a hammer with a "crumple zone", i.e., a portion more easily compressed than the rest of the hammer. The presence of a crumple zone effectively absorbs some of the shock of the hammer 48 contacting the anvil 62. Continued distal movement of the inner rod member 30 relative to the hammer element 48 causes the distal end portion 64a of the push rod block 64 to spread the expandable arms 50A outward into the expansion cutouts 44A provided in the central bore 44. Distal end portion 64a is then free to move distally between arms 50A until it engages cutouts 84 formed on the inner facing surfaces of arms 50A. Thus, the cutting blade 52, mounted atop the push rod block 64, is moved distally, relative to the hammer element 48, and travels along the cutout portion 68 in the region directly beneath the aperture 76 of the blade cover 74 so as to cut any sutures 300 which extend between the securing member 100 and the aperture 76 of the blade cover 74 (FIG. 9). Thus, in this embodiment of the present invention a single stroke of inner rod member 30 effectively deforms securing member 100 and severs excess suture material.

When released, the pivotable handle member 26 retracts to its initial rest position (FIG. 1), which in turn retracts the inner rod member 30 towards the handle assembly 12. Proximal movement of the inner rod member 30 effectuates corresponding proximal movement of the push rod member 50, which causes the push rod block 64 and the cutting blade 52 to move in a proximal direction with the hammer element 48. Because the push rod block 64 and the hammer element 48 am engaged, they move in a corresponding proximal direction, therein causing the releasing of the securing member 100 from the tool assembly 16, via the aperture 77 (FIG. 10).

Referring now to FIGS. 4–9 in conjunction with FIG. 1, the surgeon first connects a tool assembly 16 having a closed wall securing member 100 releasably disposed therein with the distal end 14a of the endoscopic body portion 14. Alternately, the instrument can be packaged with the tool assembly 16 and securing member 100 detachably connected to the endoscopic body portion 14. Turning to FIGS. 4 and 5, the surgeon next moves a suture end 300, which is already positioned in body tissue, extracorporeally, via a cannula assembly 302 (FIG. 4) and threads the end of the suture 300 through the securing member 100 in the tool assembly 16 using a conventional threading tool 304.

Thereafter, the surgeon, while grasping the ends of the suture 300 threaded through the securing member 100, inserts the tool assembly 16 and a distal end portion of the elongated body portion 14 into the body cavity 306, via a cannula assembly 302, and into approximation with body tissue 308 having the sutures 300 extending therefrom (FIG. 6). The surgeon then gently pulls proximally on the suture ends 300 extending from the body cavity 306 so as to bring the tissue pieces 308 together (FIG. 7), therein tensioning the suture material 300 extending from the body tissue 308. The surgeon then actuates the pivotable handle member 26 to deform the securing member 100 so as to maintain the suture material 300 extending from the tissue pieces in their present tensioned state.

Referring to FIG. 9, further actuation of the pivotable handle member 26 effectuates the cutting blade 52 in the tool assembly 16 to cut the unsecured lengths of suture material 300 extending from the compressed securing member 100. After full actuation of the pivotable handle member 26, the pivotable handle member 26 is returned to its initial rest position, wherein, as fully set forth above, the securing member 100 releases from the tool assembly 16 (FIG. 10).

The surgeon then removes the tool assembly 16 from the body cavity 306, via a cannula assembly 302. If the surgeon wishes to apply another securing member 100, he disengages the tool assembly 16 from the elongated body portion 14 as described above. A new tool assembly 16 having a securing member 100 releasably disposed therein is then detachably connected to the distal end portion 14A of the elongated body portion 14 as described above. The surgeon is then prepared to repeat the above described method.

Figure 26:
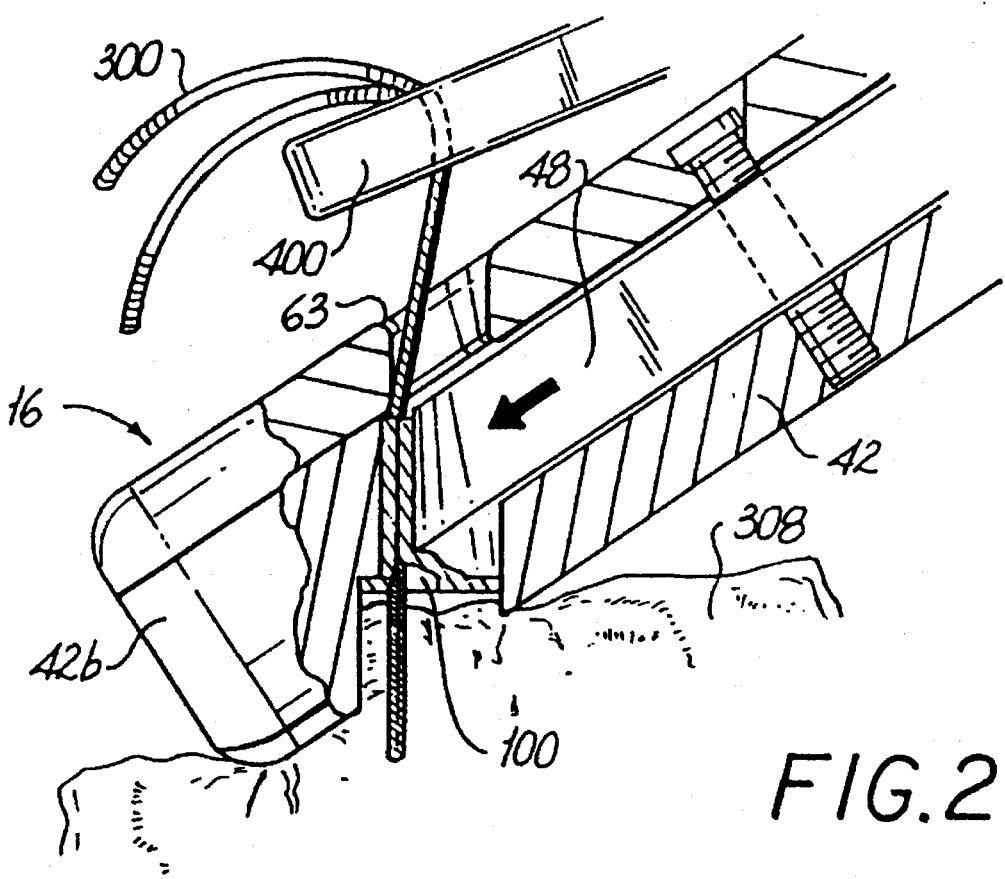
FIG. 26 is a perspective view of the tool assembly illustrated in FIG. 25, wherein the hammer element deforms the open-walled securing member about a length of suture material extending from body tissue.

Use of the open-walled securing member and instrument is illustrated in FIGS. 24, 25 and 26. As shown in FIG. 24, the surgeon first engages a length of suture material 300 through body tissue 308 which is to be joined together. After which, the surgeon introduces the tool assembly 16 along with the distal end portion of the elongated body portion 14 of the surgical apparatus 10 into approximation with the body tissue 308 having the sutures 300 extending therefrom. Referring to FIG. 25, the surgeon then threads the open-walled securing member 100A intracorporeally, such that the length of suture material 300 extending from the body tissue 308 is received through the threading channel 263 defined in the tool assembly 16 and through the open wall of the securing member 100A, thereafter receiving into the inner channel 110 of the open-walled securing member 100A releasably disposed in the anvil portion 62 of the tool assembly 16.

The surgeon may intracorporeally tension the length of suture material extending from the body tissue parts 308 so as to bring such tissue parts 308 into approximation with each other (FIG. 24). This intracorporeal tension can be accomplished by introducing a conventional grasping tool 400 into the body cavity, via a cannula assembly (not shown) wherein the grasping tool 400 can engage the suture material 300 extending from the body tissue parts 308 and subsequently tension the suture material 300 so as to effect the adjoining or approximation of the tissue parts 308.

In reference to FIG. 26, after the surgeon has effected a desired tension upon the suture material 300 extending from the tissue parts 308, the surgeon moves the pivoting handle member 26 into approximation with the stationary handle member 24 (FIG. 1) which, in turn, remotely actuates the hammer element 48 to deform the open-walled cinch member 100 about the suture material 300 in the anvil portion 62 of the tool assembly 16 so as to maintain the suture material 300 extending from the body tissue parts 308 to remain in its prescribed tensioned condition. After full proximal movement, the pivoting handle member 26 returns to its initial rest position, wherein the deformed open-walled cinch member 100 is released from the tool assembly 16 (FIG. 13).

It should be noted that the instrument can be provided without a cutting member. In this instance, a separate cutting implement is used to cut the suture.

Figure 12:
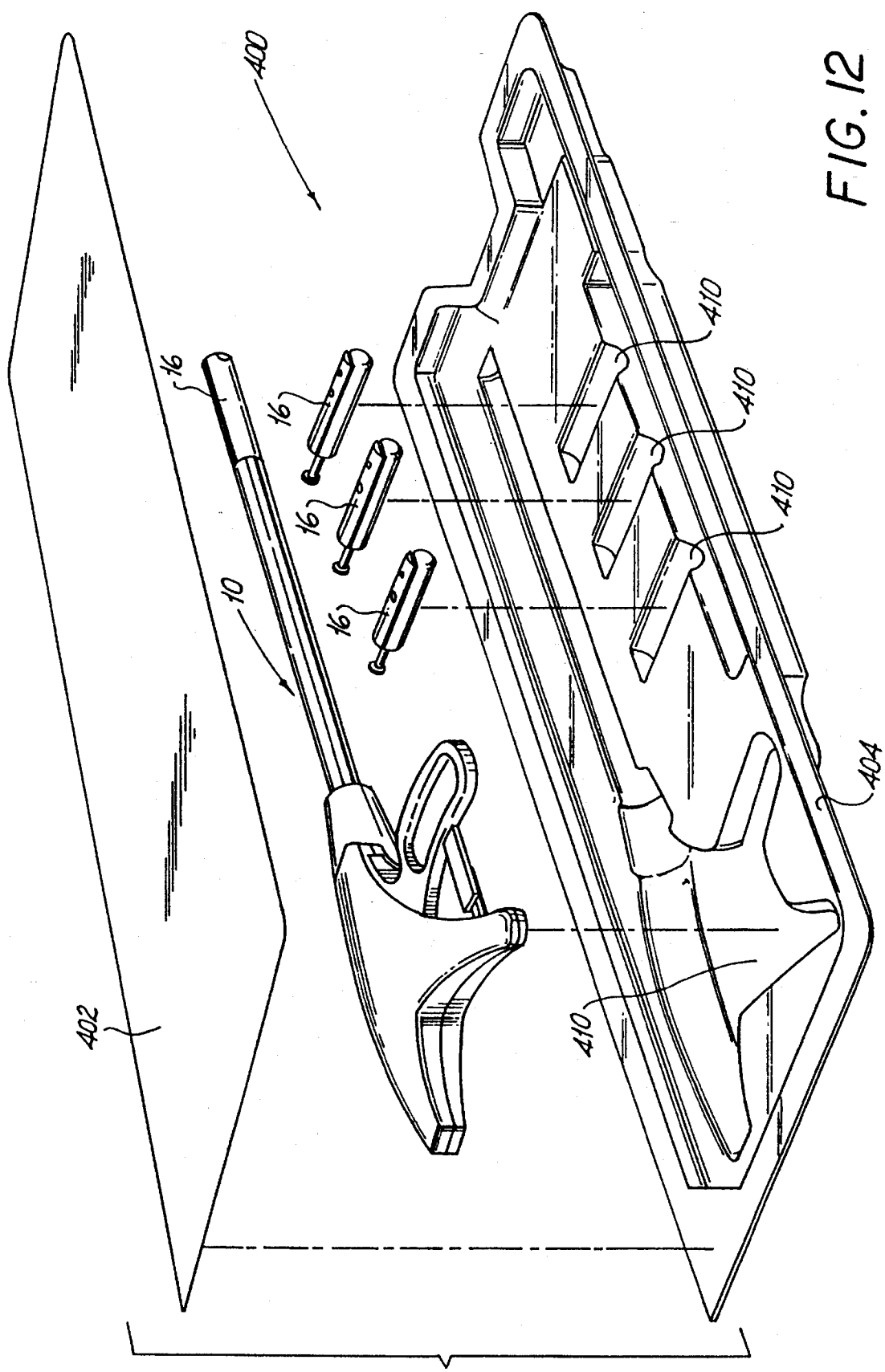
FIG. 12 is a perspective view illustrating the packaging device for the kit of the present invention.

Referring now to FIG. 12, an instrumentation kit in accordance with the present invention is designated generally at 400. The preferred embodiment of the kit 400 includes the surgical apparatus 10 having a tool assembly 16 detachably engaged therewith. At least one more additional tool assembly 16 having a securing member 100 releasably disposed therein is provided for the surgical apparatus 10 in the kit 400. It is to be appreciated that a multiplicity of tool assemblies 16 may be provided in each kit 400 for each surgical apparatus 10 provided therein. The surgical apparatus 10 and the at least one tool assembly 16 are contained in a package which includes a first cover 402 fabricated of a planar material such as Tyvek, which provides for sterilization after packaging, and a second vacuum-formed plastic cover 404 which encloses and displays the surgical apparatus 10 and at least one tool assembly 16. The vacuum-formed cover provides recesses 410 which correspond substantially in shape and dimensions in cooperation with the surgical apparatus 10 and the at least one tool assembly 16 packaged therein. Additionally, at least one of the covers is preferably transparent to provide an unobstructed view of the instrumentation packaged therein.

While the invention has been particularly shown and described with reference to the preferred embodiments, it will be understood by those skilled in the art that various modifications in form and detail may be made therein without departing from the scope and spirit of the invention. Accordingly, modifications such as those suggested above, but not limited thereto, are to be considered within the scope of the invention.

What is claimed is:

1. A surgical apparatus for applying a securing member to a length of suture material comprising:

(a) a handle assembly;

(b) an elongated body portion extending distally from said handle assembly and defining a longitudinal axis, said elongated body portion including a driving member movable by said handle assembly in a direction along the longitudinal axis;

(c) a deforming assembly extending from a distal end portion of said elongated body portion in a direction of the longitudinal axis, said deforming assembly being driven by said driving member;

(d) a suture securing member positioned in said deforming assembly, said deforming assembly remotely operable from said handle assembly, by movement of said driving member in the direction along the longitudinal axis, for enclosing and deforming said securing member to secure said securing member upon said length of suture material; and (e) a cutting member movably mounted relative to said deforming assembly for automatically cutting a length of suture extending from said securing member after said securing member has been deformed by said deforming assembly, said cutting member actuable by said handle assembly.

2. A surgical apparatus as recited in claim 1, wherein said deforming assembly and said cutting member are provided in a tool assembly detachably engageable with a distal end portion of said elongated body portion.

3. A surgical apparatus as recited in claim 1, wherein said securing member comprises a cylindrical member having first and second opposed ends and a compressible surface portion defining an inner bore portion extending between said first and second opposed ends.

4. A surgical apparatus as recited in claim 3, wherein said inner bore portion is provided with a textured surface.

5. A surgical apparatus as recited in claim 1, wherein said securing member is provided with at least one atraumatic shaped end portion.

6. A surgical apparatus as recited in claim 1, wherein said securing member is mushroom-shaped.

7. A surgical apparatus for applying a securing member to a length of suture material comprising:

(a) a handle assembly;

(b) an elongated body portion extending distally from said handle assembly and defining a longitudinal axis, said elongated body portion including a driving member movable by said handle assembly in a direction along the longitudinal axis;

(c) a tool assembly extending from a distal end portion of said elongated body portion in a direction of the longitudinal axis, said tool assembly being driven by said driving member; and (d) a suture securing member positioned in said tool assembly, said tool assembly remotely operable from said handle assembly, by movement of said driving member in a direction along the longitudinal axis, for enclosing and deforming said securing member to secure said securing member upon said length of suture material, said tool assembly being detachably connected to said elongated body portion.

8. A surgical apparatus as recited in claim 7, wherein said securing member has an opening in an outer surface portion to receive the suture material.

9. A surgical apparatus as recited in claim 7, wherein said securing member is mushroom-shaped.

10. A surgical apparatus as recited in claim 7, wherein the tool assembly includes an anvil portion and hammer element for deforming the securing member against the anvil portion.

11. A surgical apparatus as recited in claim 7, wherein the tool assembly is detachably connected to said body portion by at least one projection on the tool assembly connecting to a corresponding recess on the elongated body portion.

12. A surgical apparatus for applying a securing member to a length of suture material comprising:

(a) a handle assembly;

(b) an elongated body portion extending distally from said handle assembly and defining a longitudinal axis, said elongated body portion including a driving member movable by said handle assembly in a direction along the longitudinal axis;

(c) a securing member having an opening on an outer surface portion; and (d) a deforming assembly configured and dimensioned to receive said securing member, said deforming assembly extending from a distal end portion of said elongated body portion in a direction of the longitudinal axis, said deforming assembly remotely operable from said handle assembly, by movement of said driving member in a direction along the longitudinal axis, for enclosing and deforming said securing member to secure said securing member upon said length of suture material.

13. A surgical apparatus as recited in claim 12, wherein said securing member includes an elongated body portion having opposed first and second ends and a compressible surface defining an elongated inner channel extending between said opposed first and second ends.

14. A surgical apparatus as recited in claim 12, wherein said securing member further includes an inwardly projecting surface portion in said inner channel of said securing member.

15. A surgical apparatus recited in claim 12, wherein said deforming assembly has an opening configured to align with the opening in the securing member.

16. A surgical apparatus for applying an atraumatic-shaped securing member to a length of suture material comprising:

(a) a handle assembly;

(b) an elongated body portion extending distally from said handle assembly and defining a longitudinal axis, said elongated body portion including a driving member movable by said handle assembly in a direction along the longitudinal axis;

(c) a securing member having an atraumatic shape; and (d) a deforming assembly configured and dimensioned to receive said atraumatic-shaped securing member, said deforming assembly extending from a distal end portion of said elongated body portion in a direction of the longitudinal axis and remotely operable from said handle assembly, by movement of said driving member in a direction along the longitudinal axis, for enclosing and deforming said securing member upon said length of suture material.

17. A surgical apparatus as recited in claim 16, wherein said securing member is mushroom-shaped.

18. A surgical apparatus as recited in claim 16, wherein said securing member is cylindrical in configuration.

19. A surgical apparatus as recited in claim 16, wherein said securing member has a detent in at least one portion of the outer surface portion.

20. A surgical apparatus as recited in claim 16, wherein said securing member has an opening on an outer surface portion.

* * * * *